US006416749B1

(12) United States Patent
Hayes, Jr. et al.

(10) Patent No.: US 6,416,749 B1
(45) Date of Patent: *Jul. 9, 2002

(54) TREATMENT FOR ONYCHOMYCOSIS TOPICALLY APPLYING SALICYLIC ACID, OPTIONALLY IN COMBINATION WITH A RETINOID

(75) Inventors: Jesse Calvin Hayes, Jr., Cleveland; Gerald R. Dever, Cordova; Thomas J. Laughlin, Germantown; Charles F. Schroer, Jr., Bartlett; Gary C. Wildman, Germantown, all of TN (US); Michael L. Caswell, Poway, CA (US)

(73) Assignee: Schering-Plough Healthcare Products, Inc., Memphis, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/244,793

(22) PCT Filed: Oct. 12, 1993

(86) PCT No.: PCT/US93/09489

§ 371 (c)(1),
(2), (4) Date: Aug. 10, 1994

(87) PCT Pub. No.: WO94/08591

PCT Pub. Date: Apr. 28, 1994

Related U.S. Application Data

(63) Continuation-in-part of application No. 08/071,130, filed on Jun. 2, 1993, now Pat. No. 5,464,610, which is a continuation-in-part of application No. 07/961,282, filed on Oct. 15, 1992, now abandoned.

(51) Int. Cl.[7] .............................................. A61K 7/043

(52) U.S. Cl. .......................... 424/61; 424/402; 424/443

(58) Field of Search ........................... 424/61, 401, 443

(56) References Cited

U.S. PATENT DOCUMENTS

| 2,165,857 | A | * | 7/1939 | Jacobowitz ................... 424/61 |
| 4,666,709 | A | * | 5/1987 | Jankewitz ..................... 424/61 |
| 4,801,458 | A | * | 1/1989 | Hidaka et al. ............... 424/443 |
| 5,004,599 | A | * | 4/1991 | Scher .......................... 424/61 |
| 5,139,570 | A | * | 8/1992 | Castroglovanni et al. ..... 424/61 |
| 5,464,610 | A |   | 11/1995 | Hayes, Jr. et al. ............ 514/59 |

FOREIGN PATENT DOCUMENTS

| WO | WO 87/02580 | 5/1987 |
| WO | WO 87 04617 | 8/1987 |
| WO | WO 88 06884 | 9/1988 |
| WO | WO 88/06884 | 9/1988 |

OTHER PUBLICATIONS

R. Craik, A Simple Treatment of Ringworm of the Nails, Brit, M.J. Feb. 1920, p. 185.

R. Logan et al., Antifungal efficacy of a combination of benzoic and salicylic acids in a novel aqueous vanishing cream formulation, J. American Academy of Dermatology, Jan. 16, 1987, No. 1, Pt. 1, pp. 136–138.

Chemical Abstracts, vol. 118, No. 8, 1993, abstract No. 66891c, Guo Yi et al., Pharmacological ointments for treatment of onychomycosis, p. 462.

(List continued on next page.)

Primary Examiner—Thurman K. Page
Assistant Examiner—S. Howard
(74) Attorney, Agent, or Firm—Robert J. Lipka

(57) ABSTRACT

A method and a medicament for treating onychomycosis. The active ingredient is salicylic acid or a salt, ester or mixture thereof in a medicament, such as a plaster preparation or a liquid preparation, optionally with a retinoid compound such as tretinoin, adapalene, manoalide, retinol, tretinate or mixtures thereof. The method comprises topically administering the active ingredient to the afflicted nail. The medicament is applied without drilling holes in the nail or periodic scraping of the nail and in the absence of an imidazole antimycotic compound.

16 Claims, 2 Drawing Sheets

OTHER PUBLICATIONS

Figure 1A:
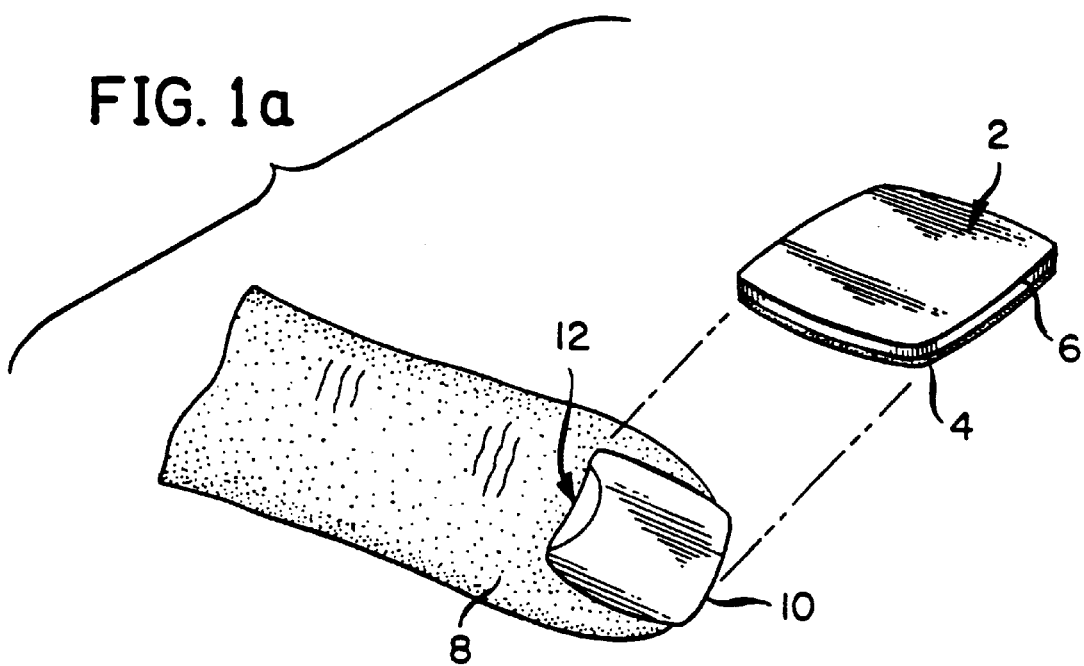

Chemical Abstracts, vol. 119, No. 8, 1993, abstract No. 79852m, D. Wolf Nail polish containing antimycotic agents.

Southeast Asian J. Trop. Med. Pub. Hlth. vol. 8, No. 1, 1977, pp. 93–98, I. Handojo et al. "The effect of topical retinoic acid(Airol) in the treatment of *Tinea versicolor*".

L. Kintish (ed.), Skin Care Update, Soap/Cosmetics/Chemical Specialties, Feb., 1995, pp. 16–22.

Wolf, Danny, *Chemical Abstracts,* vol. 119, 1193, p. 490, #79852m.*

Merck, *Encycloped. of Drugs and Chem.* 8th ed., p. 930.*

* cited by examiner

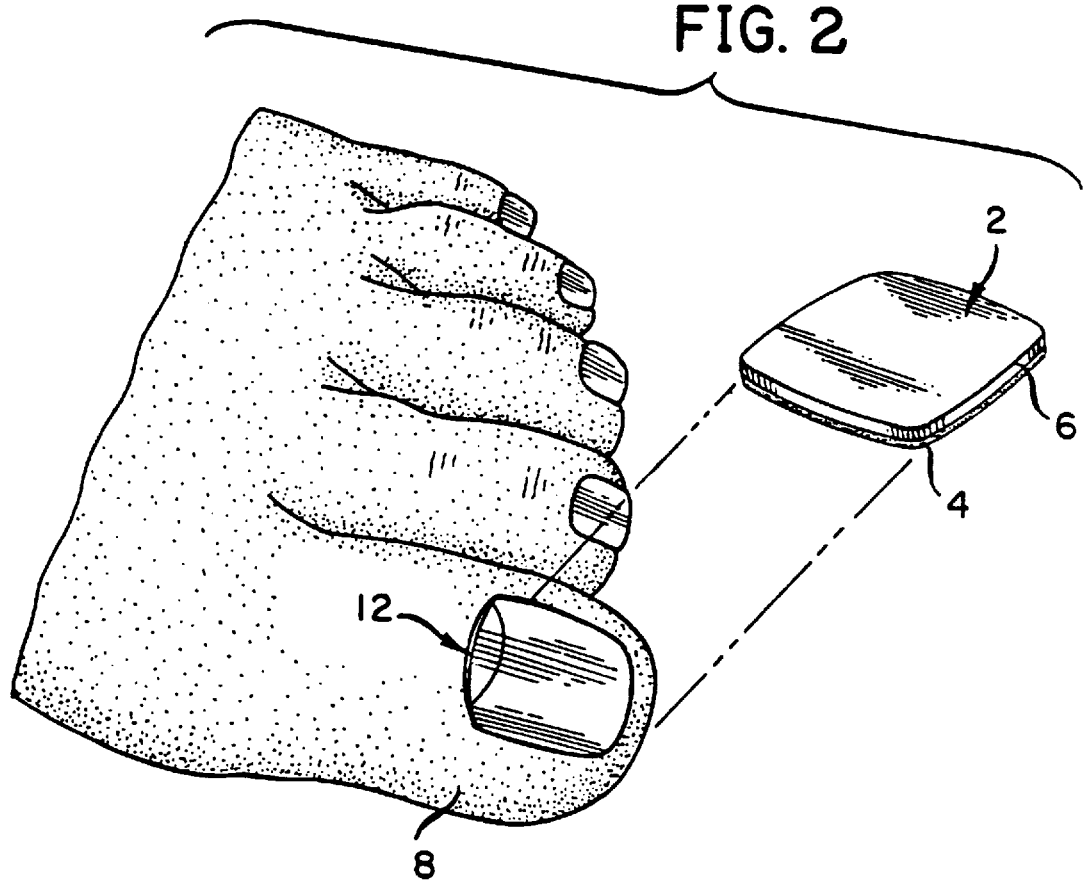

TREATMENT FOR ONYCHOMYCOSIS TOPICALLY APPLYING SALICYLIC ACID, OPTIONALLY IN COMBINATION WITH A RETINOID

The present application is the United States national application corresponding to International Application No. PCT/US 93/09489, filed Oct. 12, 1993 and designating the United States, which PCT application is in turn a continuation-in-part of U.S. application Ser. No. 07/961,282, filed Oct. 15, 1992 and U.S. application Ser. No. 08/071,130 filed Jun. 2, 1993 now U.S. Pat. No. 5,464,610, the benefit of which applications are claimed pursuant to the provisions of 35 U.S.C. 120, 363 and 365 (C).

BACKGROUND

Onychomycosis or tinea unguium (ringworm of the nails or fungal nail) is a chronic disease of the nails due to parasitic fungi. Onychomycosis can cause the nail to appear thickened and lusterless, and often causes nail discomfort. Also, the infected nail harbors a reservoir of pathogenic organisms which can spread to and reinfect other parts of the body, causing chronic diseases such as onychomycosis in other nails, athletes foot, toot dry skin and the like. Onychomycosis is prevalent throughout a large proportion of the population, with most of those afflicted from the ages of 40 years and older. To date, the United States Food and Drug Administration (FDA) has not approved any topical treatments for onychomycosis, either prescription or over-the-counter (OTC), due to the poor response of treatments evaluated. This poor response is partly because the nail is a difficult barrier for anti-fungal compounds to penetrate. In the Federal Register, Tuesday, Mar. 23, 1982, Part III Department of Health and Human Services, Food and Drug Administration, Topical Antifungal Drug Products for Over-the-Counter Human Use, Establishment of a Monograph reports: "Fungal infections of the . . . nails tend to be chronic. They respond poorly to topical therapy, partly because of the thickness of the nails . . . sites of infection provide inaccessible locations for fungi, thus drastically decreasing the penetration of topical antifungals. For this reason, OTC topical antifungals must be labeled that they are not effective for the treatment of ringworm of the . . . nails." The United States Food and Drug Administration recently re-affirmed its position in the ACTIONS: Final rule, Federal Register, Thursday, Sep. 2, 1993, 21 CFR Part 310, "Antifungal, Anorectal, and Nail Biting and Thumbsucking Deterrent Drug Products; Rules."

The research by Jacob Brem, "Treating Onychomycosis," The Lancet, Oct. 29, 1977, Vol 2., p. 937 demonstrates the extreme measures taken by one researcher to penetrate the nail: ", . . . five or six holes are drilled in the nail plate, in the form of a crescent . . . Anaesthesia is not necessary. However, the introduction of the needle is felt when the nail bed is reached . . . The holes are enlarged by dipping a round toothpick in dichloroacetic acid and drilling through the hole in the nail. When the acid reaches the nail bed a burning sensation is felt . . . A week later, five or six new holes are drilled . . . If necessary, more holes could be drilled and further applications of acid could be given."

In a similar manner, the book, "Diseases of the Nail" by V. Pardo-Castello, Thomas Books, Baltimore, Maryland, (1936), pp. 22–40 describes several treatments for onychomycosis, including the following: "Craik (43) has reported two cases treated with success by means of daily applications of a solution of 4 grams of salicylic acid in 45 c.c. of methylated spirit, after thoroughly scraping the nail. The cited reference, R.Craik, "A Simple Treatment of Ringworm of the Nails", Brit. M. J. February 1920, p. 185 describes a procedure wherein a lotion containing salicylic acid was ". . . to be painted on after scraping [the finger nail] every night, and without scraping every morning, and to be used for three months or longer." Scraping a finger nail each day for three months or more has effect of thinning or completely removing the nail plate.

Avulsion or surgical approaches for treating onychomycosis have also been used. Infected nails are treated by surgically or chemically removing the nail and treating the exposed nailbed with topical antifungals. These treatments must be continuted until the nail grows out, typically 6 months or more. Although the surgical approach generally results in cure rates significantly higher than those reported for topical treatments, most patients dislike undergoing surgery, which can result in permanent nail loss.

International Application WO 88/06884 teaches treating nail mycosis with a pharmaceutically effective amount of a topical antimycotic such as an imidazole compound, optionally with an antiseptic as exemplified using about 5% salicylic acid in a liquid preparation. There is no suggestion in this reference that salicylic acid, by itself, can serve as the antimycotic active ingredient. Nor does this reference suggest the unexpected and surprising discovery that salicylic acid, applied topically, will penetrate into the nail and exert an antifungal effect, in the absence of an imidazole antimycotic agent.

U.S. Pat. No. 5,004,599 to Scher teaches that tretinoin, also known as all-trans retinoic acid or Vitamin A acid, can promote growth of the nail unit, for purposes of improving cosmetic appearance. However, this reference offers no hint or suggestion of using tretinoin to treat a fungal nail disease such as onychomycosis. To date, the United States Food and Drug Administration (FDA) has not approved any topical treatments for onychomycosis, either prescription or over-the-counter (OTC).

Clearly, there is a need to provide an effective method for treating onychomycosis in which an active ingredient can be applied topically to an afflicted nail, without the need to drill holes in the nail, scrape the nail daily for three months or more and/or avulse the nail. There is also a need to provide a method for treating onychomycosis through use of a medicated device or a film-forming liquid preparation which enables the salicylic acid to remain in contact with the nail, thus facilitating its penetration into the nail.

SUMMARY OF THE INVENTION

The present invention is directed toward the use of salicylic acid or a salt, ester, or mixture thereof for the manufacture of a medicament to treat onychomycosis (fungal nail) by topical application to a nail, without drilling holes in the nail or periodic scraping of the nail and in the absence of an imidazole antimycotic compound. The salicylic acid can be in a medicament which is either a plaster preparation or a liquid preparation.

In another embodiment, the present invention is directed toward a medicament for treating onychomycosis without drilling holes in the nail or periodic scraping of the nail and in the absence of an imidazole antimycotic compound. The medicament comprises salicylic acid, or a salt, ester, or mixture thereof for topical application to a nail. Optionally, the medicament may also contain retinoid compound for promoting nail growth. Salicylic acid and retinoid may also be combined in a kit comprising in separate containers in a single package, salicylic acid, or a salt, ester, or mixture thereof and a retinoid compound. In the kit, preferably salicylic acid and the retinoid are in separate containers for liquid preparations.

In yet another embodiment, the present invention is directed towards a method for treating onychomycosis of an afflicted nail of a mammal without drilling holes in the nail or periodic scraping of the nail and in the absence of an imidazole antimycotic compound, by topically administering, either:

i) a medicated device comprising an active ingredient which is salicylic acid or a salt, ester or mixture thereof in a plaster preparation and the salicylic acid is present in the plaster preparation in an amount effective to treat onychomycosis; or ii) a liquid preparation comprising an active ingredient which is salicylic acid or a salt, ester or mixture thereof in a film-forming liquid vehicle, and the salicylic acid is present in the liquid preparation in an amount in an amount effective to treat onychomycois.

Optionally, the method can be practiced by combining a retinoid compound with the salicylic acid in the medicated device or liquid preparation.

Preferably the salicylic acid is employed in a plaster preparation using self-adhesive rubber or acrylic-based plaster vehicle.

The present invention has the advantage of providing an easy-to-use method for treating onychomycosis in which the afflicted nail can be treated directly, as compared to indirect or systemic methods utilizing oral antifungal agents. By directly treating the afflicted nail, fewer side effects can be expected compared with oral antifungal agents. The present method can also provide for convenient, continuous delivery of the active ingredient (ie. salicylic acid) over the treatment period. When a medicated device is employed, the method can provide further advantages in that: i) a medicated device made of a plaster and/or its carrier can be constructed to occlude and hydrate the nail for assisting delivery of the active ingredient from the plaster and promote penetration into the nail, due in part, to the increased permeability of the nail; ii) a medicated device can retain the active ingredient in place despite rubbing or scraping of the medicated device against hosiery or the shoe; iii) a medicated device has little or no odors compared with solvent-based systems; iv) a medicated device can be easily applied by placing it in contact with a nail, and can also be easily removed by peeling it off when finished; and v) a medicated device can theoretically hold greater amounts of the active ingredient since it can be made thicker than a solvent-based lacquer application.

IN THE FIGURES

FIG. 1a depicts a side view of medicated device 2 before its application to finger 8. Medicament or device 2 is made of plaster preparation 4 which is attached to carrier 6. Plaster preparation 4 contains salicylic acid or a salt, ester or mixture thereof in a plaster vehicle, such an an acrylic-based plaster vehicle. Optionally, plaster preparation 4 can also contain a retinoid compound. In this embodiment the the plaster preparation possesses self-adhesive properties so that the device can be adhered directly to nail 10 and/or nail fold 12 of finger 8 without the need for additional adhesive.

Figure 1B:
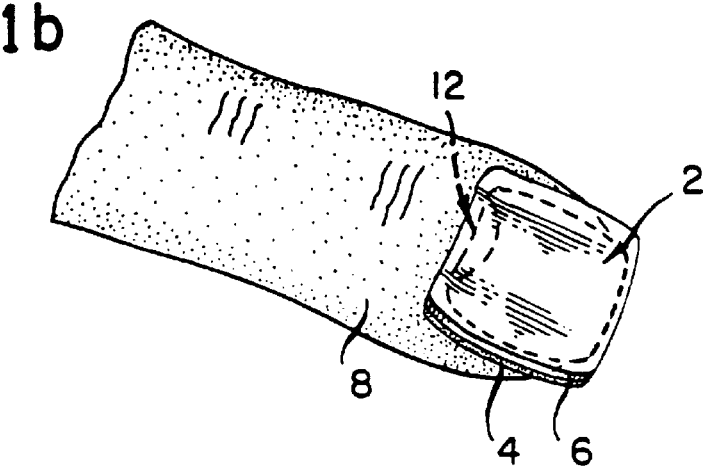

FIG. 1b depicts a perspective view of device 2 adhered directly to nail 10 and nail fold 12 of finger 8.

FIG. 2 shows a perspective view of medicated device 2 before its application only to the nail of toe 8. As in FIGS. 1a and 1b, device 2 is made of plaster preparation 4 and carrier 6. Alternatively, a bandage (not shown) could be used to further secure medicated device 2 to finger 8 or toe 8.

DETAILED DESCRIPTION OF THE INVENTION

Salicylic acid, salts or esters thereof can be employed as the active ingredient in the present method. Suitable salts include the sodium, potassium, calcium or magnesium salts thereof. Suitable esters include the C-1 to C-4 esters thereof, such as methyl salicylate. Other esters include salsalate (salicylsalicylic acid), the salicylate ester of salicylic acid. Most preferably the acid form is employed as the active ingredient.

The term "medicated device" refers to a combination of salicylic acid or a salt, ester or mixture thereof in a plaster preparation. Optionally and preferably, the plaster preparation is attached to a carrier.

The term "vehicle" broadly refers to any inert medium in which the active ingredient is administered, including but not limited to film-solvents, plasters, carriers or binders for the active ingredient.

The term "plaster" refers to any non-liquid vehicle which can be applied to the nail and which can hold the salicylic acid against the nail surface. Suitable plaster vehicles include plasters or preformed films based upon rubbers, acrylics, polyvinylalkylethers, gels or impregnated microporous membranes. Alternatively, the plaster could be combined with or formed into shape of an artificial or fake nail to improve cosmetic appearance.

The term "plaster preparation" refers to a preparation of salicylic acid or a salt, ester or mixture thereof in a plaster vehicle. The salicylic acid in a plaster preparation is employed in an amount effective to penetrate the nail to reduce and/or control onychomycosis. Such amounts can range from about 10 to about 80 percent salicylic acid by weight of the preparation, preferably from about 15 to about 60 percent by weight of the preparation, more preferably from about 20 to about 40 percent by weight of the preparation, most preferably about 40 percent by weight. Preferably, the plaster preparation is self-adhesive, ie. self-adhering to the nail, although any suitable means such as a bandage could be used to hold the plaster against the nail surface.

In the most preferred embodiment, the plaster preparation containing salicylic acid and the plaster vehicle is attached to a carrier to form a medicated device. In the medicated device, the carrier can impart occlusive properties and dimensional strength to the plaster preparation. The carrier can also provide dimensional stability to the plaster preparation against disintegration and/or tearing by external forces, such as shear forces exerted on the plaster from normal handling or from rubbing of the toenail against the shoe, sock or stocking. The carrier can be selected from a wide range of materials, especially those which can promote occlusion and hydration of the nail, such as a resin-impregnated woven cloth, flexible polyvinyl chloride film or a flexible polyester film. However, the plaster preparation can be designed to be highly occlusive without the need for the carrier to possess substantial occlusive properties. The carrier can be attached to the plaster preparation by lamination techniques, by coextrusion or by bonding the carder onto the plaster preparation using adhesives. The carrier also serves the function of directing the salicylic acid toward the nail, thus minimizing its dissipation or dispersion into the shoe interior. The medicated device can be formed into any shape suitable for administering the salicylic acid to the nail. Such shapes include but are not limited to disks, squares, rectangles or nail-shaped. The medicated device can be applied to the nail and/or nail fold singly or in combination with other medicated devices. A representative medicated device containing salicylic acid is commercially available as Dr. Scholl's Corn Removers, Schering-Plough Healthcare Inc., Memphis Tennessee.

The term "film-forming liquid" refers to a vehicle which can assume the shape of a container or flow out of a container, such as solutions of polymeric resins which upon evaporation of the solvent, will form films which hold the salicylic acid against the nail surface. Representative film forming vehicles include collodion, ie. an about 4% solution of nitrocellulose in ether-alcohol mixture of 3:1 ratio of volumes can be employed. A lower polyvinyl alcohol, propylene glycol or a lower molecular weight polyethylene glycol can be added to the vehicle to improve the elasticity of the film coating.

The term "liquid preparation" refers to a preparation of salicylic acid or a salt, ester or mixture thereof in a film-forming liquid vehicle. The salicylic acid in a liquid preparation is employed in an amount effective to penetrate the nail to reduce and/or control onychomycosis. Such amounts can range from about 6 to about 35 percent by weight of the preparation, more preferably about 10 to about 25 percent by weight, most preferably from about 12 to about 18 percent.

The phrase "without periodic scraping" refers to a treatment whereby the nail is not scraped at periodic intervals, for example, daily for three months or longer.

The amount of salicylic acid applied to the nail, either in a film-forming liquid preparation or in the device can range from about two to about 36 milligrams/square centimeters (mg/cm$^2$) of nail, preferably from about 18 to about 36 mg/cm$^2$, more preferably about 18 mg/cm$^2$.

Where a retinoid compound is optionally employed, suitable retinoid compounds include tretinoin, adapalene, manoalide, retinol, tretinate or mixtures thereof. The retinoid compounds described herein can be employed in their acid form (or alcohol form with retinol) or in any other suitable derivative, such as their esters. Suitable esters include the acetate esters or the $C_2$ to $C_8$ alkyl esters, such as ethyl, propyl, isopropyl, hexyl, octyl and the like. The amount of retinoid compound in the preparation can vary between about 0.025 and 40% of the preparation, preferably from about 0.025 to about 5–10%, more preferably from about 0.025 to about 0.5%.

Optionally, other ingredients can be employed in the topical preparation to assist penetration of salicylic acid into the nail. Such agents can include nail softeners and avulsers, such as urea, sulfhydryl agents and sulfur-based reducing agents such as sodium sulfide, nail penetration enhancers, and occluding agents and/or hydrophillic fillers to promote hydration of the nail.

Medicated devices or liquid preparations containing salicylic acid, can be topically applied to the entire surface of the nail structure, including the region of the cuticle proximal to the nail fold which overlies the growth center of the nail known as the matrix.

The medicated device or liquid preparation can be topically applied according to a regimen effective to reduce or treat onychomycosis. Generally, the preparation can be applied to the nail daily or for intermittent intervals, such as for two to three times per week. The duration of treatment can vary greatly, depending upon the degree of severity of the infection, the part of the body where the nail is being treated, the age of the person, the thickness of the nail, the rate of nail growth and the like. Generally, the toenails of a younger person can be expected to receive treatments up to 6 months, whereas the toenails of an older person can be expected to receive treatment up to about one year. These periods reflect the time required for toenails to completely grow out of the toe. Treatment of fingernails can be expected to be faster, since fingernail growth is approximately twice as fast as toenail growth. Effectiveness of the treatment can be evaluated by the subsidence or disappearance of symptoms. Less severe cases where only part of the distal portion of the nail is infected can be expected to require less time for treatment.

In animals, it may be necessary to apply the formulation with greater frequency in order to compensate for loss due to activity of the animal. In order to simplify the topical application of the preparation in humans, its use can also be effected by nail polishes, moistened pads or immersion of the nails in liquid solutions.

EXAMPLE 1

Medicated disk-shaped devices containing 40% salicylic acid in a plaster preparation are prepared by initially blending salicylic acid with a rubber-based vehicle to form a rubber-based plaster preparation. Using a coating machine with lamination stations, the plaster preparation is coated onto a release liner to form a film (ie. plaster) containing about 13 milligrams of salicylic acid per square centimeter. The film is laminated onto a carrier and prepared as rollstock. The rollstock is diecut into 8 mm diameter medicated disk-shaped devices having a surface area of 0.36 square centimeters and a thickness of 9 mils.

EXAMPLE 2

A zone of inhibition assay is performed on the plaster disks of Example 1 containing 40% salicylic acid. The zone of inhibition is recorded in millimeters (mm) from the outer edge of the disk to the margin of the area where microbial growth occurs. The results are provided in Table 1.

TABLE 1

| ORGANISM | Diameter of Zone of Inhibition - 40% salicylic acid in plaster preparation |
|---|---|
| *Staphylococcus aureus* | 12 mm |
| *Escherichia coli* | 10 mm |
| *Pseudomonas aeruginosa* | 9 mm |
| *Staphyloccus epidermidis* | 16 mm |
| *Candida albicans* | 11 mm |
| *Candida parapsilosis* | 16 mm |

The results indicate that the medicated disk-shaped devices containing 40% salicylic acid in a plaster preparation exhibit bactericidal/fungicidal activity against the organisms tested.

EXAMPLE 3

Medicated disk-shaped devices containing 40% salicylic acid are die-cut from rollstock prepared by laminating a rubber based plaster preparation containing 40% salicylic acid onto a resin-coated cloth carrier. The medicated devices have a surface area of 0.36 square centimeters. Three disks analyzed for salicylic acid content are found to have 12.72±0.36 mg/cm$^2$. These samples represent the initial amount of salicylic acid in the disks at zero hours (initial).

Fingernails of a human subject are selected which do not have holes drilled into them and which are not scraped. Disks are applied to central portion of each of three fingernails. The disks are held in place with a bandage and are removed after either 8, 24, or 48 hours. The disks removed at 24 hours are replaced with four subsequent 24-hour applications.

After contacting the nail, the disks are extracted with tetrahydrofuran and analyzed for salicylic acid by a liquid chromatographic techniques. The amount of salicylic acid released into the nail is calculated from the difference between the amount of salicylic acid initially in the disk and the amount remaining in the disk after contacting with the nail. Results are provided in Table 2.

The presence of the salicylic acid in fingernails is monitored qualitatively by observing fluoresence using a Wood's light having a short wave ultra-violet (UV) wavelength of 254 nanometers (nm).

TABLE 2

In Vivo Release of Salicylic Acid into Fingernails from Medicated Devices

| Medicated Device Applied to Nail After | Salicylic Acid Released from Medicated Device ($mg/cm^2$) | Salicylic Acid Released from Medicated Device (%) |
| --- | --- | --- |
| 0 hours (initial) | 0.00 | 0 |
| 8 hour application | 1.11 | 8.7 |
| First 24 hour application | 2.86 | 22.5 |
| 2nd 24 hour application | 3.17 | 24.9 |
| 3rd 24 hour application | 3.50 | 27.5 |
| 4th 24 hour application | 1.92 | 15.1 |
| 5th 24 hour application | 5.42 | 44.6 |

The results indicate that salicylic acid is released into the nails. Based upon zero-order release kinetics, the release rate is relatively constant over time, regardless of the number of applications. Salicylic acid is released into the nails at a mean release rate of 0.14 $mg/cm^2/hr$. The treated nails fluoresce in center of the nail, where the plaster is initially applied, with an intensity proportional to the length of exposure. Fluorescence within the nail is observed even after 5 weeks post-treatment. Five to six weeks after application of the medicated device, the area of fluorescence has moved toward the tip of the nail.

We claim:

1. A method for treating onychomycosis of an afflicted fingernail or toenail of a human without drilling holes in the nail or daily scraping of the nail and in the absence of an imidazole antimycotic compound, by topically administering, either:
   i) a medicated device comprising an active ingredient which is salicylic acid or a salt, ester or mixture thereof in a plaster preparation and the salicylic acid is present in the plaster preparation in an amount effective to treat onychomycosis; or
   ii) a liquid preparation comprising an active ingredient which is salicylic acid or a salt, ester or mixture thereof in a film-forming liquid vehicle, and the salicylic acid is present in the liquid preparation in an amount effective to treat onychomycosis.

2. The method of claim 1 wherein the amount of salicylic acid ranges from about 6 to about 35% by weight of the liquid preparation.

3. The method of claim 1 wherein the amount of salicylic acid ranges from about 10 to about 25% by weight of the liquid preparation.

4. The method of claim 1 wherein the amount of salicylic acid ranges from about 12 to about 18% by weight of the liquid preparation.

5. A method for treating onychomycosis of an afflicted fingernail or toenail of a human without drilling holes in the nail or daily scraping of the nail and in the absence of an imidazole antimycotic compound, by topically administering a preparation comprising an active ingredient comprising salicylic acid or a salt, ester or mixture thereof, such that the amount of salicylic acid applied to the nail ranges from about 18 to about 36 milligrams per square centimeter ($mg/cm^2$) of nail.

6. A method for treating onychomycosis of an afflicted fingernail or toenail of a human without drilling holes in the nail or daily scraping of the nail and in the absence of an imidazole antimycotic compound, by topically administering, either:
   i) a medicated device comprising salicylic acid or a salt, ester or mixture thereof in combination with a retinoid compound in a plaster preparation and the salicylic acid is present in the plaster preparation in an amount effective to treat onychomycosis and the retinoid compound is present in an amount effective to promote nail growth; or
   ii) a liquid preparation comprising salicylic acid or a salt, ester or mixture thereof in combination with a retinoid compound in a film-forming liquid vehicle, wherein the salicylic acid is present in the liquid preparation in an amount in an amount effective to treat onychomycosis and the retinoid is present in an amount to promote nail growth.

7. The method of claim 6 wherein the salicylic acid and the retinoid compound are topically applied in a plaster preparation.

8. The method of claim 7 wherein the retinoid compound is retinol.

9. The method of claim 7 wherein the amount of retinoid compound in the plaster preparation ranges from about 0.025 to about 40%.

10. The method of claim 7 wherein the amount of retinoid compound in the plaster preparation ranges from about 0.025 to about 10%.

11. The method of claim 7 wherein the amount of retinoid compound in the plaster preparation ranges from about 0.025 to about 0.5%.

12. The method of claim 6 wherein the salicylic acid and the retinoid compound are topically applied in the liquid preparation.

13. The method of claim 12 wherein the retinoid compound is retinol.

14. The method of claim 12 wherein the amount of retinoid compound in the liquid preparation ranges from about 0.025 to about 40%.

15. The method of claim 12 wherein the amount of retinoid compound in the liquid preparation ranges from about 0.025 to about 10%.

16. The method of claim 12 wherein the amount of retinoid compound in the liquid preparation ranges from about 0.025 to about 0.5%.

* * * * *